(12) United States Patent
Törmälä et al.

(10) Patent No.: US 6,183,479 B1
(45) Date of Patent: *Feb. 6, 2001

(54) INSTALLATION TOOL FOR SUTURE ANCHOR

(75) Inventors: Pertti Törmälä ; Eija Pirhonen, both of Tampere (FI)

(73) Assignee: Bionx Implants, Oy, Tampere (FI)

( * ) Notice: Under 35 U.S.C. 154(b), the term of this patent shall be extended for 0 days.

This patent is subject to a terminal disclaimer.

(21) Appl. No.: 09/346,146

(22) Filed: Jul. 9, 1999

Related U.S. Application Data

(63) Continuation of application No. 08/861,930, filed on May 22, 1997, now Pat. No. 5,957,924.

(51) Int. Cl.⁷ .................................................. A61B 17/58
(52) U.S. Cl. ............................. 606/104; 606/72; 606/232
(58) Field of Search ............................... 606/104, 72, 73, 606/74, 75, 139, 145, 147, 232; 112/169, 80.03

(56) References Cited

U.S. PATENT DOCUMENTS

| | | | |
|---|---|---|---|
| 5,100,417 | * 3/1992 | Cerier et al. | 606/139 |
| 5,207,679 | * 5/1993 | Li | 606/72 |
| 5,217,486 | * 6/1993 | Rice et al. | 606/72 |
| 5,354,298 | * 10/1994 | Lee et al. | 606/72 |
| 5,411,523 | * 5/1995 | Goble | 606/104 |
| 5,431,670 | * 7/1995 | Holmes | 606/147 |
| 5,782,865 | * 7/1998 | Grotz | 606/104 |
| 5,957,924 | * 9/1999 | Tormala et al. | 606/72 |

* cited by examiner

Primary Examiner—Pedro Philogene
(74) Attorney, Agent, or Firm—Kenyon & Kenyon

(57) ABSTRACT

A tool for installing a suture anchor which supports first and second suture segments having free ends, the tool including an installation end adapted to accommodate the suture anchor and to transmit mechanical power for driving the suture anchor, and a guiding arrangement adapted to guide and support the first and second suture segments in a non-parallel configuration at the installation end. The guiding arrangement may include at least one suture guide adapted to support the first and second suture segments, respectively, at least at a first and a second support points, which are spaced laterally with respect to a direction of installation of the suture anchor.

20 Claims, 4 Drawing Sheets

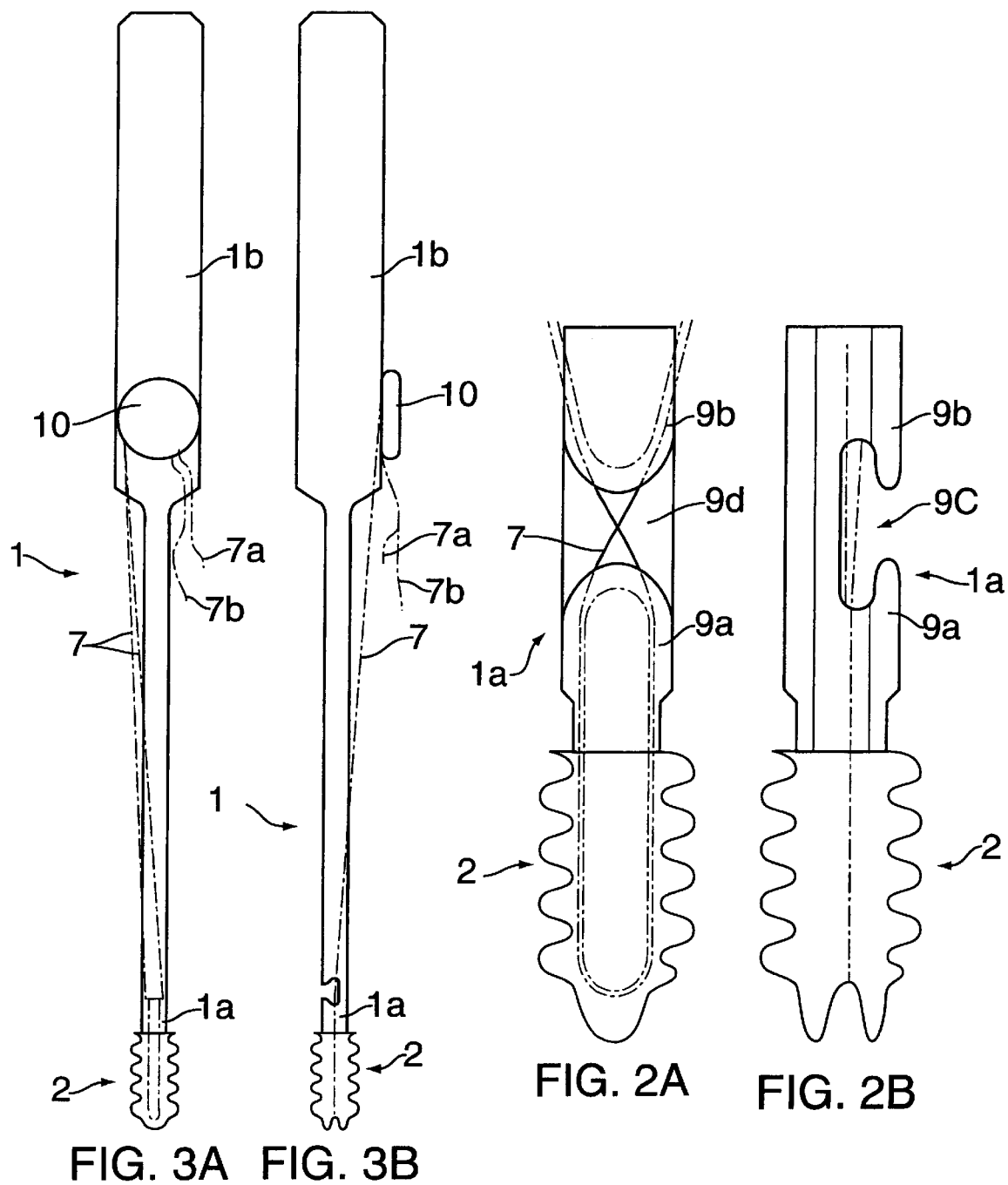

INSTALLATION TOOL FOR SUTURE ANCHOR

This application is a continuation of prior application Ser. No. 08/861,930, filed on May 22, 1997, now U.S. Pat. No. 5,957,924.

FIELD OF THE INVENTION

The present invention relates generally to installation of suture anchors and, more particularly, to a tool for installing suture anchors.

BACKGROUND OF THE INVENTION

Suture anchors are widely used in surgery, particularly for attaching sutures to bones in orthopedic surgical procedures. The suture anchor connects a portion of a suture to a bone, while the remainder of the suture (typically, two segments extending from the suture anchor) is used for various applications, e.g., for securing loosened connective tissue, such as ligament, to the bone. The suture anchor is typically driven into a hole made in the bone, e.g., into a pre-drilled hole. Suture anchors are particularly useful for firmly attaching sutures to bones during and after orthopedic surgery.

Suture anchors and tools for installing suture anchors are described in U.S. Pat. Nos. 5,207,679, 5,411,523 and 5,217,486, and in PCT publication WO 96/28100.

U.S. Pat. No. 5,411,523 describes a suture anchor and installation tool combination. The suture is threaded through a ring attached to a removable link member which is connected to an installation end of the installation tool. The threaded suture is folded into two free-ended segments which are guided together through a single bore formed in the installation tool. By applying a driving force to the installation tool, the suture anchor is driven into a pre-drilled hole in the bone together with a portion of the suture.

PCT publication WO 96/28100 also describes a suture anchor installation tool, wherein the suture is attached to the suture anchor and two free-ended segments of the suture are guided together through the installation tool. The suture anchor is driven into the bone by a force which is transmitted thereto by the installation tool.

Likewise, both U.S. Pat. Nos. 5,207,679 and 5,217,486 describe an installation tool for a suture anchor. In the devices described in these patents, the suture is threaded through a loop which is attached to the suture anchor and the installation tool drives the suture anchor into a pre-drilled hole, but the free ended segments of the suture are not guided through the installation tool.

Each of the prior art devices described above is susceptible to the effect of lateral forces which may act on the suture anchor and/or on the installation tool during installation. In response to such lateral forces, the installation tool may skew with respect to the suture anchor and/or the suture anchor may skew in the pre-drilled hole. Consequently, the suture anchor and/or the installation tool may be damaged and the suture anchor may be improperly installed in the bone.

Further, in prior art devices, a certain degree of freedom between the suture anchor and the installation tool may result in lateral movement of the suture anchor upon installation. Such lateral movement makes it difficult to align the suture anchor with respect to the pre-drilled hole. Thus, installation of a suture anchor is generally difficult and requires very high precision. Additionally, there is often insufficient space for maneuvering the installation tool at the installation site to compensate for lateral movement of the suture anchor.

SUMMARY OF THE INVENTION

Accordingly, it is an object of the present invention to overcome the drawbacks of prior art tools for installing suture anchors. More specifically, the present invention provides a suture anchor installation tool which makes the installation of suture anchors simpler and more reliable, reducing the risk of damaging the suture anchors or the installation tool.

In the present invention, a suture anchor supporting first and second suture segments is mounted on an installation end of an installation tool. The installation end includes an arrangement for transmitting mechanical power to the suture anchor to drive the suture anchor into a bone. The installation tool further includes a guiding arrangement which guides and supports the first and second suture segments near the installation end in a non-parallel configuration, wherein the distance between the first and second suture segments changes near the installation end. For example, in some embodiments of the invention, the paths of the first and second suture segments are crossed near the installation end.

The non-parallel configuration of the suture segments near the installation end of the present invention enables, inter alia, compensation for lateral forces which may act on the suture anchor and/or the installation end during installation. When the suture segments are tensioned, e.g., by pulling their free ends, the forces applied to the installation end by the first and second suture segments have opposite lateral components. However, the longitudinal components of the forces applied by the first and second suture segments are both operative to pull the suture anchor against the installation end. Thus, by controlling the relative tensions of the suture segments in the present invention, it is possible to counteract lateral forces acting on the suture anchor and/or the installation end, while maintaining the suture anchor securely mounted on the installation end. For example, when a lateral force tilts the suture anchor in the direction of the first suture segment, the tension in the second suture segment is increased relative to the first suture segment and, thus, the suture anchor is urged back to its original position. Similarly, when a lateral force tilts the suture anchor in the direction of the second suture segment, the tension in the first suture segment is increased relative to the second suture segment and, thus, the suture anchor is urged back to its original position.

In one embodiment of the present invention, the guiding arrangement includes a suture guide which supports the first and second suture segments, respectively, at least at a first and a second support points which are laterally spaced with respect to a direction of installation of the suture anchor. Thus, at the suture guide, the first and second suture segments are separated laterally by a predetermined distance. A non-parallel configuration of the suture segments near the installation end is obtained by guiding the suture segments closer together downstream of the suture guide.

In another embodiment of the present invention, the guiding arrangement includes a first and a second, longitudinally spaced, suture guides having a predetermined gap therebetween. The first suture guide supports the first and second suture segments, respectively, at least at a first and second support points which are laterally spaced with respect to the direction of installation of the suture anchor. The second suture guide supports the first and second suture segments, respectively, at least at a third and a fourth support points which are laterally spaced with respect to the direction of installation of the suture anchor. A non-parallel configuration of the suture segments is obtained by crossing the suture segments at a region between the first and second suture guides, such that the paths of the first and second suture guides are inverted. To position the suture segments in such a crossed configuration, the suture segments can be simply inserted through the gap between the first and second suture guides. This obviates the need for difficult and precision-demanding procedures for positioning the suture, such as threading through eyes or the like, which are utilized in prior art devices.

The installation tool of the present invention may be provided with a position guide which ensures correct positioning of the suture anchor on the installation end. The position guide may include a protrusion on the installation end adapted to fit into a notch on the suture anchor, or vice versa.

The suture anchor of the present invention may be formed with a peripheral, longitudinal groove which extends along two opposite sides of the suture anchor. A middle portion of the suture is placed in the peripheral groove such that it does not protrude from the surface of the suture anchor, thereby avoiding damage to the suture during installation. The remainder of the suture forms the first and second free-ended suture segments, which extend from the suture anchor. Thus, the first and second suture segments are separated by a distance substantially equal to the thickness of the suture anchor. This distance can then be changed by the suture guiding arrangement, as described above, to provide the non-parallel configuration.

The installation tool of the present invention may include two longitudinal grooves which extend along opposite sides thereof. These grooves are used for guiding the first and second suture segments, separately, downstream of the guiding arrangement to the other end of the installation tool, where the suture segments can be tensioned to tighten the mounting of the suture anchor and/or to compensate for lateral forces as described above. After being appropriately tensioned, the suture segments may be fixed to the installation tool.

In the present invention, the suture is utilized to firmly attach the suture anchor to the installation end of the installation tool. Further, the suture is utilized to counteract lateral forces which may act on the suture anchor and/or the installation end during installation. Such lateral forces are particularly apparent when a screw-in, e.g., threaded, type suture anchor is used. Since the suture anchor of the present invention is firmly mounted on the installation tool, it is easy to screw the suture anchor into a pre-drilled hole in the bone in an orthopedic procedure. The guiding arrangement firmly supports the suture segments in the non-parallel configuration during installation. The present invention is suitable for any type of suture anchor known in the art, for example, a threaded, screw-in type suture anchor or a barbed, press-in type suture anchor, as are known in the art. Further, the present invention is suitable for installing biostable suture anchors, for example, titanium suture anchors, as well as bioabsorbable suture anchors, for example, reinforced polymeric bioabsorbable suture anchors, as are known in the art.

BRIEF DESCRIPTION OF THE DRAWINGS

The present invention will be understood and appreciated more fully from the following detailed description of preferred embodiments of the invention taken in conjunction with the accompanying drawings of which:

FIG. 2A is a schematic, front view, illustration of the suture anchor and installation tool of FIG. 1A;

FIG. 2B is a schematic, side view, illustration of the suture anchor and installation tool of FIG. 1A;

FIG. 3A is a schematic, front view, illustration of the installation tool and suture anchor of FIG. 1A, showing the fill length of the installation tool;

FIG. 3B is a schematic, side view, illustration of the installation tool and suture anchor of FIG. 1A, showing the full length of the installation tool.

DETAILED DESCRIPTION OF PREFERRED EMBODIMENTS

Figure 1A:
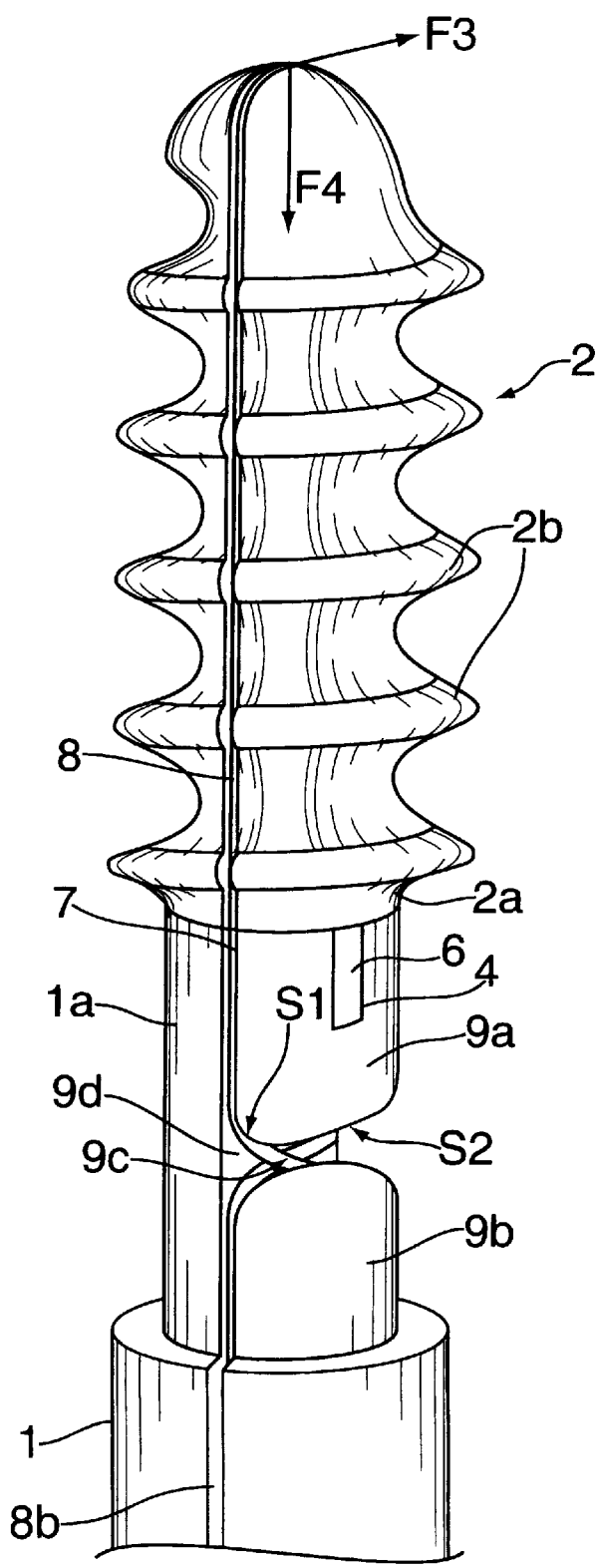
FIG. 1A is a perspective view illustration of a suture anchor operatively mounted on an installation end of an installation tool in accordance with an embodiment of the present invention.
Figure 1B:
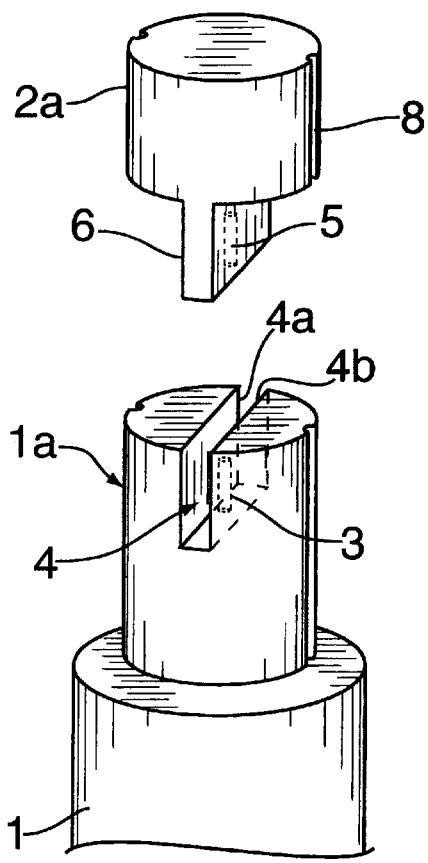
FIG. 1B is a perspective view illustration of a portion of a suture anchor and a portion of an installation tool in accordance with an embodiment of the present invention.
Figure 2C:
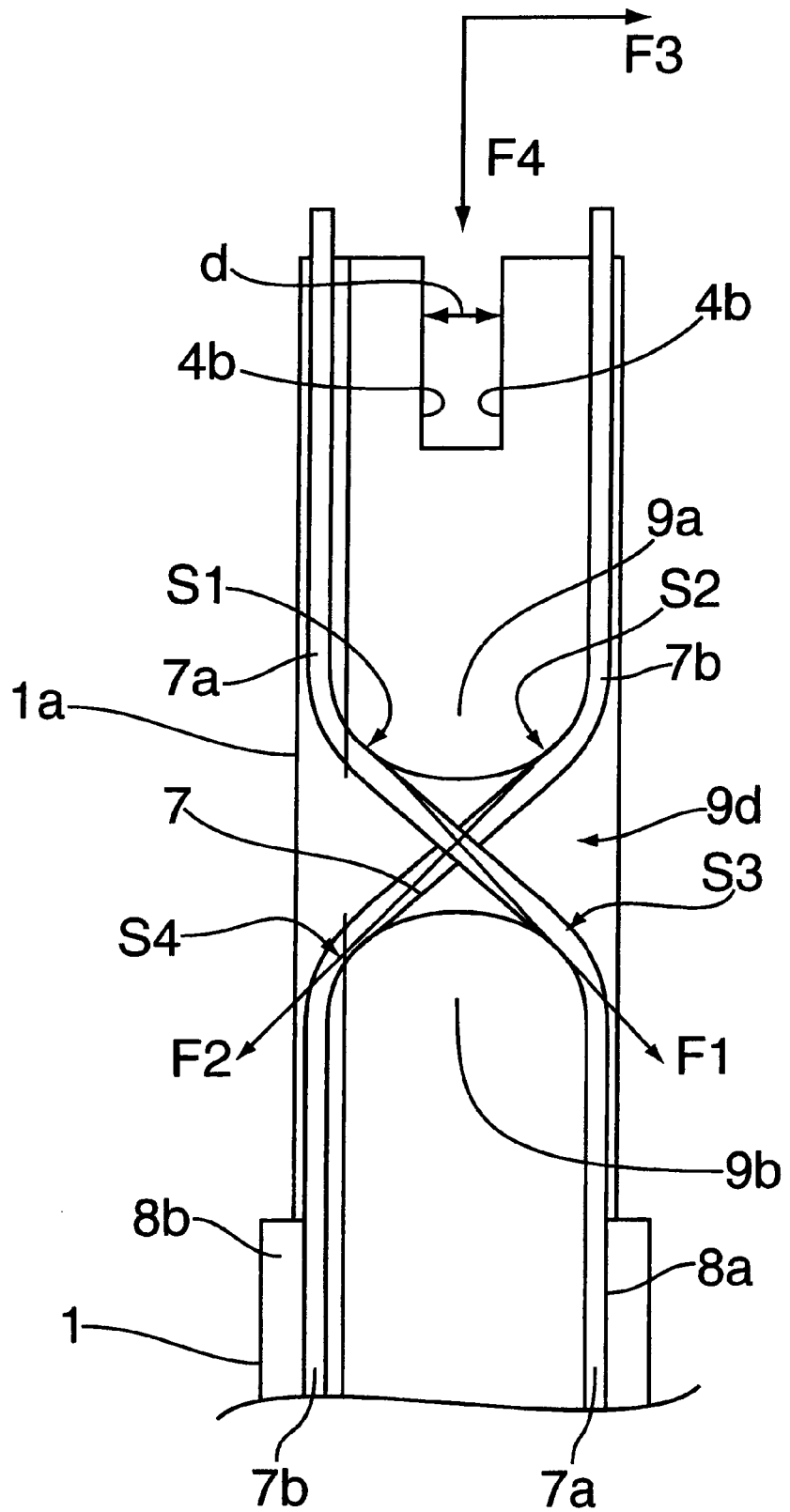
FIG. 2C is a partial, cross-sectional, illustration of part of the installation tool of FIG. 1A.

Reference is made to FIGS. 1A, 1B, 2A, 2B and 2C. FIG. 1A schematically illustrates a suture anchor 2 and a suture 7 operatively mounted on an installation tool 1 having an installation end 1a, in accordance with an embodiment of the present invention. FIGS. 2A and 2B schematically illustrate a front view and a side view, respectively, of installation suture anchor 2 mounted on installation end 1a of tool 1a Suture 7 is mounted in a peripheral groove 8 which extends along two opposite sides of suture anchor 2, as described below. Suture anchor 2 has a driving end 2a including a shaft 6 to which mechanical power, e.g., rotational power, is applied for driving the suture anchor into a bone. In the embodiment of FIG. 1A, suture anchor 2 has a threading 2b for screwing the suture anchor into a pre-made hole, e.g., a pre-drilled hole, in the bone.

FIG. 2C illustrates a cross section of installation end 1a of installation tool 1. Installation end 1a includes a cavity 4 having inner walls, 4a and 4b, which operatively engages shaft 6 of driving end 2a. Inner walls 4a and 4b of cavity 4 are preferably substantially planar and parallel. The thickness of shaft 6 is preferably substantially equal to the distance, d, between inner walls 4a and 4b, thereby to minimize the freedom of movement of shaft 6 when seated in cavity 4.

FIG. 1B schematically illustrates installation end 1a of tool 1 and driving end 2a of suture 2 in a dismounted configuration. According to an embodiment of the present invention, cavity 4 is formed with a protrusion 3 which may be located on either of inner walls 4a or 4b. Protrusion 3 is adapted to fit into a notch 5 formed on shaft 6 when shaft 6 is seated in cavity 4. Thus, protrusion 3 and notch 5 are operative to ensure correct positioning of suture anchor 2 on installation end 1a.

According to an embodiment of the present invention, suture anchor 2 is driven into the bone by rotating installation tool 1. The rotation of installation tool 1 is transmitted by cavity 4 of installation end 1a to shaft 6 of driving end 2a. When rotated, suture anchor 2 advances in the pre-drilled hole by virtue of threading 2b, as is known in the art.

It should be appreciated by a person of ordinary skill in the art that the arrangement of protrusion 3 and notch 5 can be replaced by any other suitable arrangement for securely positioning suture anchor 2 on installation tool 1. Further, more than one protrusion 3 and notch 5 can be used or the protrusion and notch can be combined with other positioning arrangements.

It should be further appreciated that cavity 4 and shaft 6 can be replaced by any other suitable arrangements for transmitting the rotation of tool 1 to suture anchor 2. However, for optimal driving of suture anchor, it is generally preferred that cavity 4 and shaft 6 have complementary shapes. For example, a quadrangular or hexagonal cavity and a complementary shaft can be used for cavity 4 and shaft 6, respectively.

In accordance with an embodiment of the present invention, suture 7 has two free ended segments, 7a and 7b, which are guided along suture anchor 2 and installation tool 1, as described below, after suture anchor 2 is positioned on installation end 1a. According to this embodiment of the invention, suture segments 7a and 7b are guided along the two opposite sides of peripheral groove 8 of suture anchor 2. Groove 8 prevents suture 7 from protruding the surface of suture anchor 2 and, thus, protects suture 7 from being damaged during the installation of suture anchor 2 in the bone. Suture anchors having peripheral guiding grooves similar to groove 8 are described in Finnish Patent application No. 965111, filed Dec. 19, 1996, assigned to the assignee of the present application, the disclosure of which is incorporated herein by reference.

In accordance with an embodiment of the present invention, installation end 1a of installation tool 1 is formed with first and second suture guides, 9a and 9b, for guiding and supporting suture 7 as described below. As shown in FIGS. 1A and 2C, suture segments 7a and 7b are guided along two opposite sides of suture guide 9a, then crossed at a region 9d, between guides 9a and 9b, and finally guided along opposite sides of suture guide 9b. As shown in FIG. 2C, suture segment 7a is supported at points S1 and S3 and suture segment 7b is supported at points S2 and S4. Suture segments 7a and 7b preferably extend beyond suture guide 9b and may be further guided along grooves 8a and 8b, respectively, formed on opposite sides of installation tool 1. Thus, in this embodiment of the invention, the paths of suture segments 7a and 7b are inverted after the suture segments are crossed at region 9d. It should be appreciated, however, that other configurations of suture segments 7a and 7b are also within the scope of the present invention. For example, if only first suture guide 9a is used, suture segments 7a and 7b are separately guided at points S1 and S2 but can be guided along a single channel downstream of points S1 and S2.

When suture segments 7a and 7b are tensioned, the tension in suture segment 7a applies a force F1 at point S1 in the direction of point S3, and the tension in suture segment 7b applies a force F2 at point S2 in the direction of point S4. Forces F1 and F2 are non-parallel and the angle between these forces can be controlled, e.g., by controlling the distance between suture guides 9a and 9b and/or the width of either or both of the suture guides. The direction of force F1 depends on the relative locations of points S1 and S3 and the direction of force F2 depends on the relative locations of points S2 and S4.

In the vicinity of suture guide 9a, forces F1 and F2 have a combined longitudinal component, F4, and a combined lateral component, F3. Longitudinal component F4 pulls suture anchor 2 towards installation end 1a and, thus, suture anchor 2 is firmly attached to installation tool 1. Since forces F1 and F2 have opposite lateral effects, the relative magnitudes of forces F1 and F2 control the direction and magnitude of lateral component F3. Thus, force F3 can be utilized to compensate for undesired lateral forces which act on installation end 1a during installation of suture anchor 2. Such compensation is not possible in prior art devices, wherein the suture segments are guided substantially in parallel at the installation end and, thus, have no lateral effect.

In an embodiment of the present invention, suture segments 7a and 7b are pre-tensioned to a predetermined, constant, tension. In this embodiment of the invention, compensation for lateral forces occurs automatically as follows. When suture anchor 2 is tilted in the direction of suture segment 7a, the tension in suture segment 7b is increased and the tension in suture segment 7a is decreased and, thus, suture anchor 2 is urged back to its original position. Similarly, when suture anchor 3 is tilted in the direction of suture segment 7b, the tension in suture segment 7a is increased and the tension in suture segment 7b is decreased and, again, suture anchor 2 is urged back to its original position.

Thus, it is a feature of the present invention that a guiding arrangement, such as suture guides 9a and 9b, is positioned at installation end 1a near suture anchor 2. To provide optimal control of the lateral forces at the installation site, support points S1 and S2 are preferably as close as possible to suture anchor 2. In some embodiments of the present invention, the distance between suture guides 9a and 9b and suture anchor 2 is smaller than or equal to the length of suture anchor 2.

Suture 7 can be conveniently mounted on installation end 1a by crossing segments 7a and 7b and pressing them towards region 9d through a gap 9c between suture guides 9a and 9b. The width of gap 9c is preferably equal to or only slightly larger than the thickness of suture 7, whereby segments 7a and 7b are conveniently inserted to region 9d and are conveniently removed therefrom, yet the suture segments cannot slip off region 9d unintentionally. This obviates the need for difficult techniques for threading suture which are required in prior art installation tools. Thus, the use of suture guides 9a and 9b and gap 9c allows efficient and convenient mounting and dismounting of suture anchor 2 and suture 7 on installation end 1a.

Reference is now made to FIGS. 3A and 3B which schematically illustrate a front view and a side view, respectively, of installation tool 1 with suture anchor 2 and suture 7 mounted thereon. As shown in FIGS. 3A and 3B, suture segments 7a and 7b, which are guided along grooves 8a and 8b, respectively, extend beyond installation end 1a to a handle portion 1b of installation tool 1, where the suture segments can be conveniently attached to installation tool 1 by wrapping them around a support member 10. Suture segments 7a and 7b are preferably tensioned as they are wrapped around support member 10 until they are securely supported by the support member. Thus, a substantially constant tension is maintained in suture segments 7a and 7b, during installation, to ensure the firm mounting of suture anchor 2 on installation tool 1. It should be appreciated that support member 10 can be replaced by any other suitable arrangement for tensioning and supporting suture segments 7a and 7b. For example, each of suture segments 7a and 7b may be supported by a separate tensioning/support arrangement, such that the tensions in segments 7a and 7b may be separately controlled.

Figure 4:
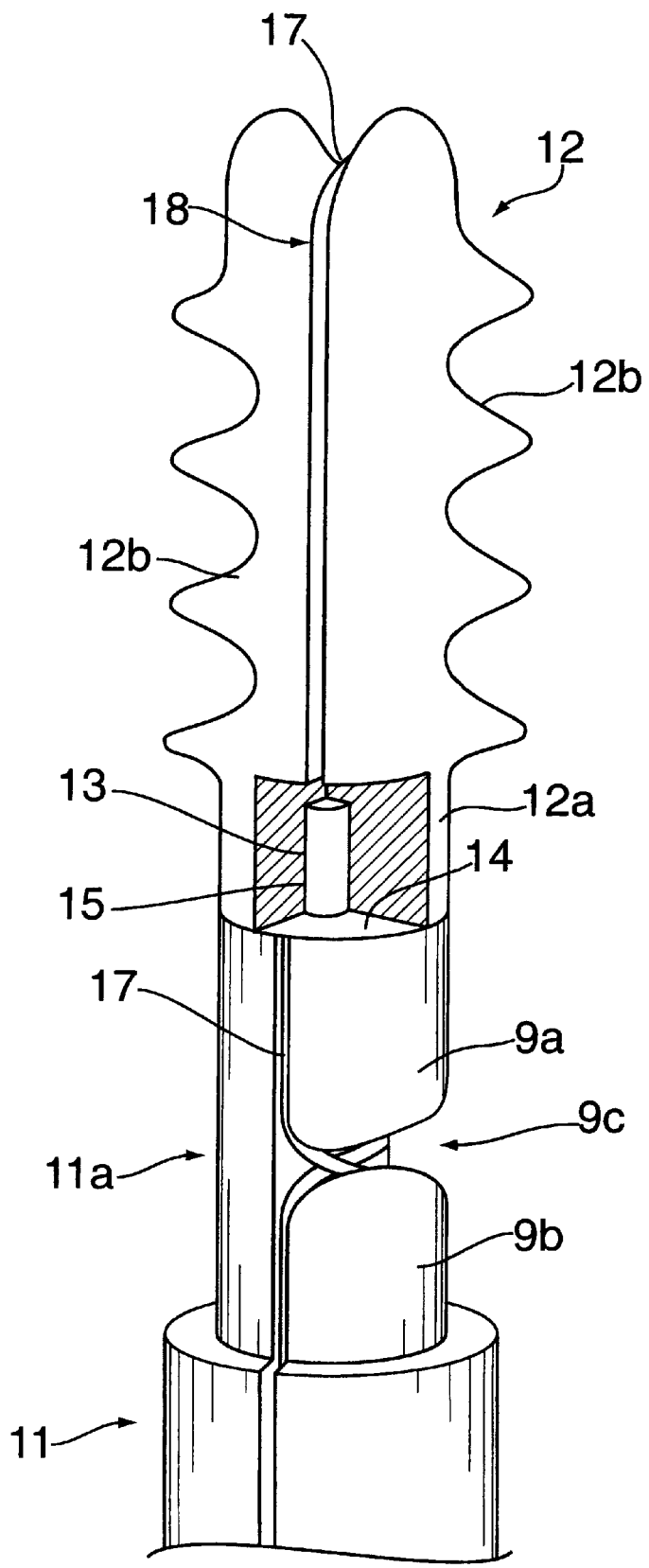
FIG. 4 is a perspective view, partly cut-away, illustration of a suture anchor operatively mounted on an installation end of an installation tool in accordance with another embodiment of the present invention.

Reference is now made to FIG. 4 which schematically illustrates a suture anchor 12 and a suture 17 operatively mounted on an installation end 11a of an installation tool 11, in accordance with another embodiment of the present invention. Suture 17 is mounted in a peripheral groove 18 which extends along two opposite sides of suture anchor 12, as described above with reference to suture 7 of FIG. 1A. Suture anchor 12 has a driving end 12a and includes a plurality of barbs or scales 12b, as are known in the art, which prevent the suture anchor from being released after installation. Thus, suture anchor 12 is adapted to be installed by pressing it into a pre-drilled hole in a bone. Accordingly, in contrast to the embodiment of FIG. 1A, installation tool 11 is not provided with means for transmitting rotational power to suture anchor 12. In the embodiment of FIG. 4, suture anchor 12 is driven into the bone by a linear force applied by a surface 14 of installation end 11a.

According to an embodiment of the present invention, installation end 11a includes a mounting/positioning rod 13 which extends from surface 14. Rod 13 is adapted to be tightly fitted in a cavity 15 formed in driving end 12a of suture anchor 12. Thus, suture anchor 12 is mounted on installation end 11a simply by inserting rod 13 into cavity 15, as is known in the art. The tight fit between protrusion 13 and cavity 15 ensures correct positioning of suture anchor 12 on installation 11a.

It should be appreciated by a person of ordinary skill in the art that the arrangement of rod 13 and cavity 15 can be replaced by any other suitable arrangement for securely positioning suture anchor 12 on installation tool 11.

Except as described above, installation tool 11 of FIG. 4 is substantially similar to installation tool 1 of FIG. 1A, whereby similar elements of installation tool 1 and installation tool 11 are denoted by the same reference numerals. Further, the mounting of suture 17 on installation tool 11, using suture guides 9a and 9b, is substantially the same as described above with reference to installation tool 1 of FIG. 1A.

It should be appreciated that the present invention is not limited to the threaded and barbed or scaled suture anchors described above and may be used in conjunction with any other type of suture anchor. Further, the present invention can be applied to biostable suture anchors, for example, titanium suture anchors, as well as to bioabsorbable suture anchors, for example, reinforced polymeric bioabsorbable suture anchors, as are known in the art.

It should be appreciated by a person of ordinary skill in the art that the present invention is not limited to the particular embodiments thus far described but, rather, the of the present invention is defined only by the following claims:

What is claimed is:

1. A tool for installing a suture anchor which supports first and second suture segments having free ends, the tool comprising:
   an installation end adapted to accommodate the suture anchor and to transmit mechanical power for driving the suture anchor; and
   a guiding arrangement adapted to guide and support the first and second suture segments in a non-parallel configuration at the installation end.

2. The tool according to claim 1 wherein said guiding arrangement comprises at least one suture guide adapted to support the first and second suture segments, respectively, at least at a first and a second support points, which are spaced laterally with respect to a direction of installation of said suture anchor.

3. The tool according to claim 2 wherein said guiding arrangement comprises first and second suture guides which are spaced along an axis of said installation end, wherein the first suture guide is adapted to support the first and second suture segments, respectively, at least at said first and second support points, and wherein the second suture guide is adapted to support the first and second suture segments, respectively, at least at a third and fourth support points, which are spaced laterally with respect to said direction of installation.

4. The tool according to claim 3 wherein the first and second suture segments are crossed at a crossing region between said first and second suture guides.

5. The tool according to claim 4 wherein said first and second suture guides are separated by a gap through which the first and second suture segments are introduced to said crossing region.

6. The tool according to claim 5 wherein the width of said gap is equal to or larger than the thickness of said suture segments.

7. The tool according to claim 1 wherein the distance between the guiding arrangement and the suture anchor is less than or equal to the length of the suture anchor.

8. The tool according to claim 2 wherein the distance between the guiding arrangement and the suture anchor is less than or equal to the length of the suture anchor.

9. The tool according to claim 3 wherein the distance between the guiding arrangement and the suture anchor is less than or equal to the length of the suture anchor.

10. The tool according to claim 4 wherein the distance between the suture anchor and said crossing region is less than or equal to the length of the suture anchor.

11. The tool according to claim 5 wherein the distance between the suture anchor and said crossing region is less than or equal to the length of the suture anchor.

12. The tool according to claim 6 wherein the distance between the suture anchor and said crossing region is less than or equal to the length of the suture anchor.

13. The tool according to claim 1 comprising a tensioning arrangement which supports the free ends of the first and second suture segments, wherein a substantially constant tension is maintained in each of the suture segments between the tensioning arrangement and said guiding arrangement.

14. The tool according to claim 2 comprising a tensioning arrangement which supports the free ends of the first and second suture segments, wherein a substantially constant tension is maintained in each of the suture segments between the tensioning arrangement and said at least one suture guide.

15. The tool according to claim 3 comprising a tensioning arrangement which supports the free ends of the first and second suture segments, wherein a substantially constant tension is maintained in each of the suture segments between the tensioning arrangement and said first suture guide.

16. The tool according to claim 4 comprising a tensioning arrangement which supports the free ends of the first and second suture segments, wherein a substantially constant tension is maintained in each of the suture segments between the tensioning arrangement and said first suture guide.

17. The tool according to claim 5 comprising a tensioning arrangement which supports the free ends of the first and second suture segments, wherein a substantially constant tension is maintained in each of the suture segments between the tensioning arrangement and said first suture guide.

18. The tool according to claim 6 comprising a tensioning arrangement which supports the free ends of the first and second suture segments, wherein a substantially constant tension is maintained in each of the suture segments between the tensioning arrangement and said first suture guide.

19. The tool according to claim 7 comprising a tensioning arrangement which supports the free ends of the first and second suture segments, wherein a substantially constant tension is maintained in each of the suture segments between the tensioning arrangement and said guiding arrangement.

20. The tool according to claim 8 comprising a tensioning arrangement which supports the free ends of the first and second suture segments, wherein a substantially constant tension is maintained in each of the suture segments between the tensioning arrangement and said at least one suture guide.

* * * * *